United States Patent
Moriguchi et al.

(10) Patent No.: US 10,017,672 B2
(45) Date of Patent: *Jul. 10, 2018

(54) HOT-MELT ADHESIVE AGENT

(71) Applicant: HENKEL AG & CO. KGAA, Duesseldorf (DE)

(72) Inventors: Masahiro Moriguchi, Osaka (JP); Naohiro Maeda, Osaka (JP)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/944,526

(22) Filed: Nov. 18, 2015

(65) Prior Publication Data
US 2016/0068723 A1 Mar. 10, 2016

Related U.S. Application Data

(63) Continuation of application No. PCT/JP2014/064041, filed on May 21, 2014.

(30) Foreign Application Priority Data

May 22, 2013 (JP) .................................. 2013-107764

(51) Int. Cl.
| C09J 153/02 | (2006.01) |
| B32B 37/12 | (2006.01) |
| A61L 15/58 | (2006.01) |
| C08L 53/02 | (2006.01) |

(52) U.S. Cl.
CPC .......... *C09J 153/02* (2013.01); *A61L 15/585* (2013.01); *B32B 37/1207* (2013.01); *C08L 53/02* (2013.01); *B32B 2037/1215* (2013.01); *C08L 2205/02* (2013.01)

(58) Field of Classification Search
CPC ...... C09J 153/02; C08L 53/02; C08L 2205/02
See application file for complete search history.

(56) References Cited

U.S. PATENT DOCUMENTS

| 5,948,527 | A | 9/1999 | Gerard et al. | |
| 2008/0070053 | A1* | 3/2008 | Schmierer | C09J 153/02 428/500 |
| 2008/0153971 | A1* | 6/2008 | Salazar | C08F 297/04 524/505 |
| 2011/0257337 | A1* | 10/2011 | Oda | C08L 53/02 525/98 |
| 2011/0263782 | A1* | 10/2011 | Dubois | C08L 53/02 524/505 |
| 2013/0030096 | A1* | 1/2013 | Lietzau | H01B 7/295 524/140 |
| 2015/0175855 | A1* | 6/2015 | Nakajima | C09J 153/02 524/505 |
| 2016/0009966 | A1* | 1/2016 | Inoue | C09J 153/02 524/505 |
| 2016/0040047 | A1* | 2/2016 | Inoue | A61L 15/585 524/505 |
| 2017/0253778 | A1* | 9/2017 | Inoue | C09J 153/02 |

FOREIGN PATENT DOCUMENTS

| CN | 101331203 A | 12/2008 |
| CN | 101547988 A | 9/2009 |
| CN | 102264854 A | 11/2011 |
| EP | 1564273 A1 | 8/2005 |
| EP | 1564275 A1 | 8/2005 |
| JP | 6210163 A | 1/1987 |
| JP | 02232049 A | 9/1990 |
| JP | 5-311138 A | 11/1993 |
| JP | 05331355 A | 12/1993 |
| JP | 9-291265 A | 11/1997 |
| JP | 10-130349 A | 5/1998 |
| JP | 2000282006 A | 10/2000 |
| JP | 2000309767 A | 11/2000 |
| JP | 2004137297 A | 5/2004 |
| JP | 2004238548 A | 8/2004 |
| JP | 20068947 A | 1/2006 |
| JP | 2007530714 A | 11/2007 |
| JP | 2009511713 A | 3/2009 |
| JP | 2010506005 A | 2/2010 |
| JP | 2010536957 A | 12/2010 |
| JP | 2012021078 A | 2/2012 |
| JP | WO2014017380 A1 | 7/2016 |
| WO | 9928405 A1 | 6/1999 |
| WO | 03027182 A1 | 4/2003 |
| WO | WO 2014/017380 * | 1/2014 |

OTHER PUBLICATIONS

Nakajima, electronic translation of WO 2014/017380.*

* cited by examiner

Primary Examiner — Jeffrey C Mullis
(74) Attorney, Agent, or Firm — Sun Hee Lehmann

(57) ABSTRACT

Problem to be solved of the present invention is to provide a hot-melt adhesive agent which is capable of applying at low temperature, excellent in adhesiveness at the wide temperature ranges (10 to 40° C.), and excellent in balance between tackiness and retention force, and a disposable product obtained by employing the hot-melt adhesive agent. Means for Solving the problem is a hot-melt adhesive agent comprising a thermoplastic block copolymer (A) which is a copolymer of vinyl class aromatic hydrocarbons and conjugated diene compounds, wherein the thermoplastic block copolymer (A) comprises the following component (A1) and component (A2): (A1) a radial type styrene block copolymer having a styrene content of 35 to 45% by weight, a diblock content of 50 to 90% by weight, and has a viscosity at 25° C. as 25% toluene solution of not more than 250 mPa·s; and (A2) a triblock type styrene block copolymer.

4 Claims, No Drawings

HOT-MELT ADHESIVE AGENT

CROSS-REFERENCE TO RELATED APPLICATION

This application is a continuation of International Patent Application No. PCT/JP2014/064041 filed May 21, 2014, which claims priority to Japanese Patent Application No. 2013-107764 filed in Japan on May 22, 2013, the contents of both of which are incorporated herein by reference.

FILED OF THE INVENTION

The present invention relates to a hot-melt adhesive agent, and more particularly to a hot-melt adhesive agent used in the field of disposable products typified by a paper diaper and a napkin.

BACKGROUND OF THE INVENTION

An adhesive agent containing a thermoplastic block copolymer as a main component has been used in disposable products typified by a paper diaper and a napkin and, particularly, a hot-melt adhesive agent based on a styrene class block copolymer has widely been used. For example, a paper diaper is produced by bonding a polyethylene film with other members (for example, a nonwoven fabric, an elastic material such as a natural rubber, a water-absorbing paper, etc.) using a hot-melt adhesive agent. The hot-melt adhesive agent can be applied to various members using various methods and, even when using any method, the hot-melt adhesive agent is melted by heating so as to obtain an appropriate viscosity, and then the molten adhesive agent is applied to various constituent members in a dot, linear, stripe, spiral or sheet form.

It is now required for the paper diaper to improve drapeness thereof, and a study has been made in improving flexibility and drapeness of the paper diaper by more thinning a polyethylene film or the above-mentioned various members such as a nonwoven fabric. Thinning of various members significantly reduces material costs. However, thinning of the polyethylene film may cause a problem that heat resistance deteriorates and application of a high-temperature (not lower than 150° C.) hot-melt adhesive agent leads to melting of the polyethylene film or formation of wrinkles of the polyethylene film. Therefore, adhesive agent manufacturers have made a progress on the development of a low-temperature-applicable hot-melt adhesive agent which is capable of applying at low temperature (not higher than 140° C.).

Taking workability and environmental aspect in the case of application of the hot-melt adhesive agent into account, manufacturers producing a paper diaper and a sanitary good strongly desire lowering of the viscosity of the hot-melt adhesive agent. The hot-melt adhesive agent commonly comprises a base polymer and a plasticizer, and a study has been made in lowering the viscosity of the hot-melt adhesive agent by a method in which the amount of the base polymer is decreased to thereby increase the amount of the plasticizer. However, the production of a paper diaper using a low viscosity hot-melt adhesive agent produced using such method may cause a problem that the balance between an adhesiveness to a polyethylene film which composes members of the paper diaper and a retention force (cohesive force) is deteriorated, and the softening point is excessively lowered.

JP 2004-137297 A discloses a hot-melt adhesive agent including a linear type styrene block copolymer, a tackifier resin and a plasticizer (claim 1). The hot-melt adhesive agent of the literature has a low viscosity, and suitable for applying at low temperature, however, is not sufficient in adhesiveness at low temperature in winter or at high temperature in summer.

JP H5 (1993)-311138 A mentions a hot-melt adhesive agent including a radial type styrene block copolymer (claim 1). However, the hot-melt adhesive agent of the JP H5 (1993)-311138 A has high melt viscosity, and are not suitable for conducting application at low temperature. The hot-melt adhesive agent is insufficient in peel strength at 40° C.

In JP 2009-511713 A, structure of the block copolymer or melting point of the tackifier resin is specified, and combination ratio of the both is further adjusted to obtain a hot-melt adhesive agent suitable for coating at low temperature (claim 1). The hot-melt adhesive agent of JP 2009-511713 A is, however, insufficient in adhesiveness at low temperature, low in tackiness, and insufficient in balance between retention force and tackiness. The hot-melt adhesive agent of JP 2009-511713 A, therefore, does not completely satisfy the high level requirements of users for use in disposable produces.

SUMMARY OF THE INVENTION

An object of the present invention is to provide a hot-melt adhesive agent which is capable of applying at low temperature, has an excellent adhesiveness at wide temperature ranges (10 to 40° C.), and is excellent in balance between tackiness and retention force, and a disposable product obtained by employing the hot-melt adhesive agent.

The present invention provides a hot-melt adhesive agent comprising a thermoplastic block copolymer (A) which is a copolymer of vinyl class aromatic hydrocarbons and conjugated diene compounds, wherein the thermoplastic block copolymer (A) comprises the following component (A1) and component (A2):

(A1) a radial type styrene block copolymer having a styrene content of 35 to 45% by weight, a diblock content of 50 to 90% by weight, and has a viscosity at 25° C. as 25% toluene solution of not more than 250 mPa·s; and (A2) a triblock type styrene block copolymer.

In one embodiment, the radial type styrene block copolymer (A1) comprises a three branched type styrene-butadiene block copolymer.

In one embodiment, the triblock type styrene block copolymer (A2) has a styrene content of 30 to 45% by weight.

In one embodiment, the thermoplastic block copolymer (A) further comprises (A3) a linear type styrene block copolymer having a diblock content of 50 to 90% by weight.

In one embodiment, the hot-melt adhesive agent further comprises a tackifier resin (B), a plasticizer (C) and a stabilizer (D).

In one embodiment, the hot-melt adhesive agent has a content of (A) of 15 to 30 parts by weight, based on 100 parts by weight of the total weight of (A) to (D).

In one embodiment, the hot-melt adhesive agent has a melt viscosity at 140° C. of not more than 4000 mPa·s.

The present invention also provides a disposable product obtained by applying any one of the above hot-melt adhesive agents.

DETAILED DESCRIPTION OF THE INVENTION

The hot-melt adhesive agent of the present invention is capable of applying at low temperature because of low melt viscosity, and is excellent in adhesiveness at wide temperature ranges (10 to 40° C.), and is also excellent in balance between tackiness and retention force (cohesive force).

The disposable product of the present invention is composed by adhering, with the hot-melt adhesive agent, the parts such as a polyethylene film and a nonwoven web, and therefore, each of the parts does not peel off even under a low temperature during the winter season, during storage in warehouse at the summer season, or under a body temperature as the disposable product is on use.

In the present invention, the "thermoplastic block copolymer (A)" is a copolymer obtained by block copolymerization of vinyl class aromatic hydrocarbons with conjugated diene compounds, and is usually a resin composition including those which include a vinyl class aromatic hydrocarbon block and a conjugated diene compound block.

As used herein, the "vinyl class aromatic hydrocarbon" means an aromatic hydrocarbon compound having a vinyl group, and specific examples thereof include styrene, o-methylstyrene, p-methylstyrene, p-tert-butylstyrene, 1,3-dimethylstyrene, α-methylstyrene, vinylnaphthalene, vinylanthracene, and the like. Particularly, styrene is preferable. These vinyl class aromatic hydrocarbons can be used alone or in combination.

The "conjugated diene compound" means a diolefin compound having at least a pair of conjugated double bonds. Specific examples of the "conjugated diene compound" include 1,3-butadiene, 2-methyl-1,3-butadiene (or isoprene), 2,3-dimethyl-1,3-butadiene, 1,3-pentadiene, and 1,3-hexadiene. Particularly, 1,3-butadiene and 2-methyl-1,3-butadiene are preferable. These conjugated diene compounds can be used alone or in combination.

The thermoplastic block copolymer (A) according to the present invention may be either an unhydrogenated product or a hydrogenated product.

Specific examples of the "unhydrogenated product of the thermoplastic block copolymer (A)" include those in which blocks based on the conjugated diene compound are not hydrogenated. Specific examples of the "hydrogenated product of the thermoplastic block copolymer (A)" include block copolymers in which blocks based on the conjugated diene compound are entirely or partially hydrogenated.

A proportion that the "hydrogenated product of the thermoplastic block copolymer (A)" is hydrogenated can be indicated by a "hydrogenation ratio". The "hydrogenation ratio" of the "hydrogenated product of the thermoplastic block copolymer (A)" refers to a proportion of double bonds converted into saturated hydrocarbon bonds by hydrogenation on the basis of all aliphatic double bonds included in the blocks based on the conjugated diene compound. The "hydrogenation ratio" can be measured by an infrared spectrophotometer, a nuclear magnetic resonance spectrometer, and the like.

Specific examples of the "unhydrogenated product of the thermoplastic block copolymer (A)" include a styrene-isoprene block copolymer (also referred to as "SIS") and a styrene-butadiene block copolymer (also referred to as "SBS"). Specific examples of the "hydrogenated product of the thermoplastic block copolymer (A)" include a hydrogenated styrene-isoprene block copolymer (also referred to as "SEPS") and a hydrogenated styrene-butadiene block copolymer (also referred to as "SEBS").

In the present invention, the thermoplastic block copolymer (A) employs both a radial type styrene block copolymer (A1) and a triblock type styrene block copolymer (A2). In the present description, the radial type styrene block copolymer is a branched styrene block copolymer having a structure in which a plurality of linear type styrene block copolymers radially project from a coupling agent as the center. The linear type styrene block copolymer is a linear copolymer in which blocks of styrene are bonded with blocks of conjugated diene. Specific structure of the radial type styrene block copolymer is shown below.

$$(S-E)_n Y \qquad (1)$$

In the formula (1), n is an integer of not less than 2, S is a styrene block, E is a conjugated diene compound block, and Y is a coupling agent. n is preferably 3 or 4, and more preferably 3. The polymer in which n is 3 is referred to as a three branched type, while the copolymer in which n is 4 is referred to as a four branched type. When n is 3 or 4, the obtained hot-melt adhesive agent exhibits low melt viscosity and high retention force (cohesive force). The conjugated diene compound is preferably butadiene or isoprene.

The radial type styrene block copolymer (A1) in the present invention is a resin composition, and includes a styrene-conjugated diene block copolymer represented by the formula:

$$(S-E) \qquad (2)$$

wherein S and E have the same meanings as defined above, in a given proportion. The styrene-conjugated diene block copolymer of the formula (2) may be sometimes called "diblock".

The coupling agent is a polyfunctional compound which radially bonds a linear type styrene block copolymer. There is no particular limitation on types of the coupling agent.

Examples of the coupling agent include a silane compound such as halogenated silane or alkoxysilane, a tin compound such as halogenated tin, an epoxy compound such as a polycarboxylate ester or epoxydized soybean oil, an acrylic ester such as pentaerythritol tetraacrylate, a divinyl compound such as epoxysilane or divinylbenzene, and the like. Specific examples thereof include trichlorosilane, tribromosilane, tetrachlorosilane, tetrabromosilane, methyltrimethoxysilane, ethyltrimethoxysilane, vinyltrimethoxysilane, vinyltriethoxysilane, tetramethoxysilane, tetraethoxysilane, tetrachlorotin, diethyl adipate, and the like.

In the present invention, the radial type styrene block copolymer (A1) has a styrene content of 35 to 45% by weight, a diblock content of 50 to 90% by weight, and has a viscosity at 25° C. as a 25% (by weight) toluene solution of not more than 250 mPa·s.

The "styrene content" refers to a proportion of a styrene block included in (A1). The styrene content is 35 to 45% by weight, and more preferably 35 to 40% by weight. The styrene content of (A1) is within the above range, whereby, the hot-melt adhesive agent of the present invention becomes excellent in balance between retention force (cohesive force), tackiness and adhesiveness at low temperature.

The "diblock content" refers to a proportion of a styrene-conjugated diene compound block copolymer of the formula (2) included in (A1). The diblock content is 50 to 90% by weight, and more preferably 55 to 85% by weight.

The diblock content of (A1) is within the above range, whereby, the hot-melt adhesive agent of the present invention becomes excellent in tackiness and adhesiveness at low temperature. The diblock content of (A1) of less than 50% by weight may sometimes cause deterioration of either adhesiveness at low temperature or tackiness of the obtained hot-melt adhesive agent because of excessive content of a branched structure component represented by the formula (1). The diblock content of (A1) of more than 90% by weight may make it difficult to enhance the retention force of the hot-melt adhesive agent even in the case of having a radial structure.

The "viscosity at 25° C. as a 25% (by weight) toluene solution" refers to a viscosity at 25° C. as a solution having a concentration of 25% by weight using toluene as a solvent, and can be measured using various viscometers, for example, a Brookfield BM-type viscometer (spindle No. 27).

The viscosity at 25° C. as a 25% (by weight) toluene solution" of (A1) is not more than 250 mPa·s, and ranges from 100 to 250 mPa·s. Particularly, the viscosity is more preferably 130 to 200 mPa·s.

In the hot-melt adhesive agent of the present invention, the viscosity at 25° C. as a 25% (by weight) toluene solution" of (A1) within the above range may cause significant decrease in melt viscosity, leading to easy application at low temperature.

HJ10, HJ12, HJ13, and HJ15 are commercially available from Asahi Kasei Chemicals Corporation as the radial type styrene block copolymer (A1).

In the present invention, the thermoplastic block copolymer (A) includes a triblock type styrene block copolymer (A2). The triblock type styrene block copolymer has a chemical structure represented by the formula:

wherein, S is a styrene block, and E is a conjugated diene block.

The triblock type styrene block copolymer is distinguished from the diblock type styrene block copolymer. That is, the triblock type styrene block copolymer has a diblock content of 0% by weight. Incorporation of triblock type styrene block copolymer (A2) enhances adhesiveness at 40° C. of the adhesive agent. The adhesive agent of the present invention includes both (A1) and (A2), and exhibits excellent adhesiveness at the wide temperature ranges (10 to 40° C.).

The triblock type styrene block copolymer (A2) has a styrene content of preferably 25 to 50% by weight, more preferably 30 to 45% by weight. The styrene content of (A2) is within the above range, whereby, the hot-melt adhesive agent is improved in adhesiveness at 40° C.

Examples of the triblock type styrene block copolymer include styrene-butadiene-styrene copolymers and styrene-isoprene-styrene copolymers. Examples of commercially available (A2) include TR 2000 (trade name), TR 2003 (trade name) manufactured by JSR Corporation; Asaprene T420 (trade name) manufactured by Asahi Kasei Chemicals Corporation; Vector 4411A (trade name), Vector 4211A (trade name) manufactured by Dexco Company.

(A1) is incorporated into (A) in an amount of 10 to 95 parts by weight, preferably 20 to 80 parts by weight, more preferably 20 to 50 parts by weight, based on 100 parts by weight of the total weight of (A). The content of (A1) is within the above range, whereby, the hot-melt adhesive agent is improved in adhesiveness at a low temperature (around 10° C.), improved in tackiness and retention force, and permitted to applying at low temperature. (A2) is incorporated into (A) in an amount of 5 to 90 parts by weight, preferably 10 to 75 parts by weight, more preferably 20 to 70 parts by weight, based on 100 parts by weight of the total weight of (A). The content of (A2) is within the above range, whereby, the hot-melt adhesive agent is improved in adhesiveness at a high temperature (around 40° C.), improved in tackiness and retention force, and permitted to applying at low temperature.

In the present invention, the thermoplastic block copolymer (A) preferably contains a linear type styrene block copolymer (A3).

In the present description, the liner type styrene block copolymer (A3) has a diblock content of 50 to 90% by weight. (A3) is clearly distinguished from (A2) since the triblock type styrene copolymer (A2) has a diblock content of 0% by weight.

Examples of the commercially available linear type styrene block copolymer (A3) include Asaprene T438 (trade name), Asaprene T439 (trade name) manufactured by Asahi Kasei Chemicals Corporation; Quintac 3270 (trade name) manufactured by Zeon Corporation.

(A3) is incorporated in (A) in an amount of up to 20 parts by weight, preferably up to 10 parts by weight, more preferably up to 5 parts by weight. The content of (A3) is within the above range, whereby, the hot-melt adhesive agent is improved in adhesiveness at 10 to 40° C.

The thermoplastic block copolymer (A) optionally includes other styrene block copolymers (A4) which do not fall in (A1) to (A3). Examples of the other styrene block copolymers (A4) include radial type styrene block copolymers having a diblock content of less than 50% by weight. Examples of the commercially available (A4) includes TR2500 (trade name) manufactured by JSR Corporation; Quintac 3460 (trade name) manufactured by Zeon Corporation.

The hot-melt adhesive agent of the present invention includes a tackifier resin (B) and a plasticizer (C). The tackifier resin is, not particularly limited as long as, that conventionally employed for a hot-melt adhesive agent, and able to provide the objective hot-melt adhesive agent of the present invention.

Examples of such tackifier resin (B) include a natural rosin, a modified rosin, a hydrogenated rosin, a glycerol ester of a natural rosin, a glycerol ester of a modified rosin, a pentaerythritol ester of a natural rosin, a pentaerythritol ester of a modified rosin, a pentaerythritol ester of a hydrogenated rosin, a copolymer of a natural terpene, a three dimensional polymer of a natural terpene, hydrogenated derivatives of a copolymer of a hydrogenated terpene, a polyterpene resin, hydrogenated derivatives of a phenol class modified terpene resin, an aliphatic petroleum hydrocarbon resin, hydrogenated derivatives of an aliphatic petroleum hydrocarbon resin, an aromatic petroleum hydrocarbon resin, hydrogenated derivatives of an aromatic petroleum hydrocarbon resin, a cyclic aliphatic petroleum hydrocarbon resin, and hydrogenated derivatives of a cyclic aliphatic petroleum hydrocarbon resin. These tackifier resins can be used alone or in combination. It is also possible to use, as the tackifier resin, a liquid type tackifier resin as long as it has a colorless to pale yellow color tone and has substantially no odor, and also has satisfactory thermal stability. When the performances are considered from a comprehensive point of view, a hydrogenated derivative of a resin and the like is preferred as the tackifier resin. An unhydrogenated tackifier resin is optionally employed in combination.

It is possible to use, as the tackifier resin (B), commercially available products. Examples of such commercially available products include ECR179EX (trade name) manufactured by Tonex Co., Ltd.; Maruka Clear H (trade name) manufactured by Maruzen Petrochemical CO, LTD.; Alcon M100 (trade name) manufactured by Arakawa Chemical Industries, Ltd.; I-MARV S100 (trade name) manufactured by IDEMITSU KOSAN CO., LTD.; Clearon K100 (trade name), Clearon K4090 (trade name) and Clearon K4100 manufactured by YASUHARA CHEMICAL CO., LTD.;

ECR179EX (trade name) and ECR231C (trade name) manufactured by Tonex Co., Ltd.; Regalite C6100L (trade name) and Regalite C8010 (trade name) manufactured by Eastman Chemical Company; and FTR2140 (trade name) manufactured by Mitsui Chemicals, Inc. Examples of the unhydrogenated tackifier resin include Quinton DX390N (trade name) and Quinton DX395 (trade name) manufactured by Zeon Corporation. These commercially available tackifier resins can be used alone or in combination.

The plasticizer (C) is blended for the purpose of decreasing melt viscosity of the hot-melt adhesive agent, imparting flexibility to the hot-melt adhesive agent, and improving wettability of the hot-melt adhesive agent to an adherend. There is no particular limitation as long as the plasticizer is compatible with the block copolymer and the objective hot-melt adhesive agent of the present invention is obtainable. Examples of the plasticizer (C) include paraffin oil, naphthene oil and aromatic oil. Colorless and odorless naphthene oil is particularly preferable.

It is possible to use, as the plasticizer (C), commercially available products. Examples thereof include White Oil Broom 350 (trade name) manufactured by Kukdong Oil & Chemicals Co., Ltd.; Diana Fresia S32 (trade name), Diana Process Oil PW-90 (trade name) and DN Oil KP-68 (trade name) manufactured by IDEMITSU KOSAN CO., LTD.; Enerper M1930 (trade name) manufactured by BP Chemicals, Inc.; Kaydol (trade name) manufactured by Crompton Corporation; Primol352 (trade name) manufactured by ESSO Corp.; Process Oil NS100 manufactured by IDEMITSU KOSAN CO., LTD.; and KN4010 (trade name) manufactured by PetroChina Company Limited, Sunpure-N90 (trade name) manufactured by Sun Oil Company, Ltd. These plasticizers (C) can be used alone or in combination.

A hot-melt agent of the present invention optionally further includes a stabilizer (D). The "stabilizer" is blended so as to prevent decrease in molecular weight, occurrence of gelation, coloration, odor and the like of the hot-melt adhesive agent due to heat, thereby improving stability of the hot-melt adhesive agent, and there is no particular limitation as long as the objective hot-melt adhesive agent of the present invention is obtainable. Examples of the "stabilizer" include an antioxidant and an ultraviolet absorber.

The "ultraviolet absorber" is used so as to improve light resistance of the hot-melt adhesive agent. The "antioxidant" is used so as to prevent oxidative degradation of the hot-melt adhesive agent. There is no particular limitation on the antioxidant and the ultraviolet absorber, as long as they are commonly used in disposable products and the below-mentioned objective disposable products are obtainable.

Examples of the antioxidant include phenol antioxidants, sulfur antioxidants and phosphorous antioxidants. Examples of the ultraviolet absorber include benzotriazole ultraviolet absorbers and benzophenone ultraviolet absorbers. It is also possible to add lactone stabilizers. These additives can be used alone or in combination.

It is possible to use, as the stabilizer (D), commercially available products. Examples thereof include SUMILIZER GM (trade name), SUMILIZER TPD (trade name) and SUMILIZER TPS (trade name) manufactured by Sumitomo Chemical Co. Ltd.; IRGANOX 1010 (trade name), IRGANOX HP2225FF (trade name), IRGAFOS 168 (trade name) and IRGANOX 1520 (trade name) manufactured by Ciba Specialty Chemicals Inc.; and JF77 (trade name) manufactured by Johoku Chemical Co., Ltd. These stabilizers can be used alone or in combination. The stabilizer is those generally employed in disposable products. Any substances may be employed, as long as it is able to provide the objective disposable products as described below, and is not particularly limited.

In the hot-melt adhesive agent of the present invention, the content of (A) is 3 to 60 parts by weight, preferably 8 to 45 parts by weight, more preferably 15 to 30 parts by weight, and particularly preferably 10 to 30 parts by weight, based on 100 parts by weight of the total weight of (A) to (D). The content of (A) is within the above range, whereby, the hot-melt adhesive agent is improved in adhesiveness at the wide temperature range (10 to 40° C.), improved in tackiness and retention force, and capable of applying at low temperature.

If necessary, the hot-melt adhesive agent according to the present invention optionally further contains the additives other than those described above, such as fine particle fillers.

The hot-melt adhesive agent of the present invention is produced by blending the above components in a given proportion, optionally blending various additives, and melting the mixture with heating, followed by mixing. Specifically, the hot-melt adhesive agent is produced by charging the above components in a melt-mixing vessel equipped with a stirrer, followed by mixing with heating.

The obtained hot-melt adhesive agent has a melt viscosity at 120° C. of preferably not more than 20,000 mPa·s, more preferably not more than 15,000 mPa·s, particularly preferably not more than 10,000 mPa·s. As to the melt viscosity at 140° C., the hot-melt adhesive agent has preferably not more than 5,000 mPa·s, more preferably not more than 4500 mPa·s, particularly preferably not more than 4000 mPa·s. In the present description, the "melt viscosity" refers to a viscosity in molten state of the hot-melt adhesive agent and is measured by a Brookfield RVT-type viscometer (spindle No. 27).

The hot-melt adhesive agent according to the present invention has low melt viscosity, that is, a melt viscosity at 120° C. of not more than 20,000 mPa·s and a melt viscosity at 140° C. of not more than 5,000 mPa·s, and therefore, is capable of applying at law temperature (not higher than 140° C.).

The hot-melt adhesive agent according to the present invention can be fed in liquid form or semi-liquid form. The hot-melt adhesive agent is preferred from the environmental point of view because it is able to be stored in a temperature keeping container in liquid form or semi-liquid form, and is able to be fed as it is. That is, generation of waste materials is able to be reduced, and power consumption is able to be saved when the hot-melt adhesive agent is produced.

The hot-melt adhesive agent according to the present invention preferably has a retention force at 40° C. of not less than 10 minutes, more preferably not less than 30 minutes, and particularly preferably not less than 50 minutes on the method for evaluation of retention force mentioned in Examples.

The hot-melt adhesive agent according to the present invention preferably has a peel strength (10° C., 20° C., 40° C.) of not less than 1,200 gf/inch (11.8 N/3.05 cm), and more preferably 1,400 gf/inch (13.7 N/3.56 cm), measured by the method for evaluation of peel strength mentioned in Examples.

The hot-melt adhesive agent according to the present invention preferably has loop tackiness of not less than 2,000 gf/inch (19.6 N/5.08 cm), more preferably 2,200 gf/inch (21.6 N/5.59 cm), measured by the method for evaluation of loop tackiness mentioned in Examples.

The hot-melt adhesive agent according to the present invention is widely used in paper processing, bookbinding, disposable products, and the like, and is mainly used in disposable products. There is no particular limitation on "disposable products" as long as they are so-called sanitary materials. Specific examples thereof include a paper diaper, a sanitary napkin, a pet sheet, a hospital gown, a surgical white garment, and the like.

The present invention provides, in another aspect, a disposable product obtained by non-contact coating of the above hot-melt adhesive agent at low temperature (not higher than 140° C.). The disposable product is constituted by bonding at least one member selected from the group consisting of a woven fabric, a nonwoven fabric, a rubber, a resin and papers with a polyolefin film using the hot-melt adhesive agent according to the present invention. The polyolefin film is preferably a polyethylene film for the reason of durability, costs and the like.

In the production line for the disposable product, the hot-melt adhesive agent is commonly applied to at least one of various members (for example, nonwoven fabric, etc.) of the disposable product, and a polyolefin film, and then the film is contact-bonded with the members to produce a disposable product. In the case of applying, the hot-melt adhesive agent may be discharged from various ejectors. In the present invention, the "non-contact coating" method refers to a coating method in which a discharger is not brought into contact with a member or a film in the case of applying the hot-melt adhesive agent.

Specific examples of the non-contact coating method include a spiral coating method capable of coating in a spiral form, an omega coating or control seam coating method capable of coating in a wavy form, a slot spray coating or curtain spray coating method capable of coating in a plane form, a dot coating method capable of coating in a dot form, and the like.

EXAMPLES

The present invention will be described for the purpose of describing the present invention in more detail and specific manner by way of Examples and Comparative Examples. These are exemplary of the present invention and are not to be considered as limiting.

In Examples, unless otherwise specified, parts by weight and percentages by weight are based on the places where a solvent is not taken into account.

Components used in the present Examples are shown below.

(A) Thermoplastic Block Copolymer
<(A1) Radial Type Styrene Block Copolymer>
(A1-1) Three branched type styrene-butadiene block copolymer (styrene content of 38% by weight, diblock content of 80% by weight, viscosity at 25° C. as 25% (by weight) toluene solution of 184 mPa·s, HJ12 (manufactured by Asahi Kasei Chemicals Corporation))
(A1-2) Three branched type styrene-butadiene block copolymer (styrene content of 39% by weight, diblock content of 80% by weight, viscosity at 25° C. as 25% (by weight) toluene solution of 165 mPa·s, HJ13 (manufactured by Asahi Kasei Chemicals Corporation))
(A1-3) Three branched type styrene-butadiene block copolymer (styrene content of 43% by weight, diblock content of 70% by weight, viscosity at 25° C. as 25% (by weight) toluene solution of 243 mPa·s, HJ14 (manufactured by Asahi Kasei Chemicals Corporation))

<(A2) Triblock Type Styrene Block Copolymer>
(A2-1) Triblock type styrene-butadiene block copolymer (styrene content of 40% by weight, diblock content of 0% by weight, viscosity at 25° C. as 25% (by weight) toluene solution of 795 mPa·s, JSR TR2000 (manufactured by JSR Corporation))
(A2-2) Triblock type styrene-butadiene block copolymer (styrene content of 43% by weight, diblock content of 0% by weight, viscosity at 25° C. as 25% (by weight) toluene solution of 688 mPa·s, JSR TR2003 (manufactured by JSR Corporation))
(A2-3) Triblock type styrene-butadiene block copolymer (styrene content of 30% by weight, diblock content of 0% by weight, viscosity at 25° C. as 25% (by weight) toluene solution of 1200 mPa·s, Asaprene T420 (manufactured by Asahi Kasei Chemicals Corporation))
(A2-4) Triblock type styrene-isoprene block copolymer (styrene content of 44% by weight, diblock content of 0% by weight, viscosity at 25° C. as 25% (by weight) toluene solution of 120 mPa·s, Vector 4411A (manufactured by Dexco Company))
(A2-5) Triblock type styrene-isoprene block copolymer (styrene content of 30% by weight, diblock content of 0% by weight, viscosity at 25° C. as 25% (by weight) toluene solution of 300 mPa·s, Vector 4211A (manufactured by Dexco Company))

<(A3) Linear Type Styrene Block Copolymer>
(A3-1) Linear type styrene-butadiene block copolymer (styrene content of 43% by weight, diblock content of 70% by weight, viscosity at 25° C. as 25% (by weight) toluene solution of 360 mPa-s, Asaprene T438 (manufactured by Asahi Kasei Chemicals Corporation))
(A3-2) Linear type styrene-isoprene block copolymer (styrene content of 43% by weight, diblock content of 60% by weight, viscosity at 25° C. as 25% (by weight) toluene solution of 170 mPa·s, Asaprene T439 (manufactured by Asahi Kasei Chemicals Corporation))
(A3-3) Linear type styrene-isoprene block copolymer (styrene content of 24% by weight, diblock content of 67% by weight, viscosity at 25° C. as 25% (by weight) toluene solution of 320 mPa·s, Quintac 3270 (manufactured by Zeon Corporation))

<(A4) Other (Radial Type) Styrene Block Copolymers>
(A4-1) Three branched type styrene-butadiene block copolymer (styrene content of 35% by weight, diblock content of 40% by weight, viscosity at 25° C. as 25% (by weight) toluene solution of 490 mPa·s, JSR TR2500 (manufactured by JSR Corporation)) (A4-2) Three branched type styrene-isoprene block copolymer (styrene content of 25% by weight, diblock content of 40% by weight, viscosity at 25° C. as 25% (by weight) toluene solution of 380 mPa·s, Quintack 3460 (manufactured by Zeon Corporation))

(B) Tackifier Resin
(B1) Hydrogenated tackifier resin (ECR179EX (manufactured by Exxon Mobil Corporation))
(B2) Hydrogenated tackifier resin (Alcon M100 (manufactured by Arakawa Chemical Industries, Ltd.))
(B3) Hydrogenated tackifier resin ((Alcon M115 (manufactured by Arakawa Chemical Industries, Ltd.)
(B4) Hydrogenated tackifier resin (I-MARV S100N (manufactured by IDEMITSU KOSAN CO., LTD.))

(B5) Hydrogenated tackifier resin (I-MARV S100 (manufactured by IDEMITSU KOSAN CO., LTD.))
(B6) Hydrogenated tackifier resin (Regalite C6100L (manufactured by Eastman Chemical Company))
(B7) Unhydrogenated tackifier resin (Quinton DX390N (manufactured by Zeon Corporation))
(B8) Unhydrogenated tackifier resin (Quinton DX395N (manufactured by Zeon Corporation))
(B9) Hydrogenated tackifier resin (ECR5615 (manufactured by Exxon. Mobil Corporation))
(B10) Liquid tackifier resin (Maruka Clear H (manufactured by Maruzen Petrochemical CO, LTD.))
(C) Plasticizer
(C1) Paraffin oil (Diana Fresis S-32 (manufactured by IDEMITSU KOSAN CO., LTD.))
(C2) Naphthene oil (Sunpure-N90 (manufactured by Sun Oil Company, Ltd))
(C3) Naphthene oil (Nyflex 222B (manufactured by Nynas CO., LTD.))
(D) Stabilizer
(D1) Phenol antioxidants (SUMILIZER GM (manufactured by Sumitomo Chemical Co., Ltd.))
(D2) Sulfur antioxidants (SUMILIZER TPD (manufactured by Sumitomo Chemical Co., Ltd.))
(D3) Benzotriazole ultraviolet absorber (JF77 (manufactured by Johoku Chemical Co., Ltd.))
(D4) Phenol antioxidants (Irganox 1010 (manufactured by BASF Company))
(E) Wax
(E1) Maleic anhydride modified polypropylene wax (Rikosen TP MA6252 (manufactured by Clariant (Japan) K.K.))

Preparation of Hot-Melt Adhesive Agents of Examples 1 to 10 and Comparative Examples 1 to 8.

The respective components were blended according to the formulations shown in Tables 1 to 4, and then melt-mixed at about 150° C. to prepare hot-melt adhesive agents. In Tables 1 to 4, "St" means a styrene content, "diblock" means a diblock content, and "TV" means a viscosity at 25° C. as a 25% (by weight) toluene solution.

TABLE 1

| | | | Example | | | | | |
|---|---|---|---|---|---|---|---|---|
| | | | 1 | 2 | 3 | 4 | 5 | 6 |
| (A) | | | | | | | | |
| (A1) | (A1-1) Three branched radial SBS (St %: 38%, diblock: 80%), TV: 184 mPas | | | | | | 5 | |
| | (A1-2) Three branched radial SBS (St %: 39%, diblock: 80%), TV: 165 mPas | | 8 | 10 | 4.5 | | 4.5 | 20 |
| | (A1-3) Three branched radial SBS (St %: 43%, diblock: 70%), TV: 243 mPas | | | | | | | |
| (A2) | (A2-1) Triblock SBS (St %: 40%, diblock: 0%), TV: 795 mPas | | 12.3 | 10.3 | 12 | 12.3 | 12.3 | 2 |
| | (A2-2) Triblock SBS (St %: 43%, diblock: 0%), TV: 688 mPas | | | | | | | |
| | (A2-3) Triblock SBS (St %: 30%, diblock: 0%), TV: 1200 mPas | | | | | | | |
| | (A2-4) Triblock SIS (St %: 44%, diblock: 0%), TV: 120 mPas | | | | | | | 5 |
| | (A2-5) Triblock SIS (St %: 30%, diblock: 0%), TV: 300 mPas | | | | | | | |
| | Total weight of (A1) and (A2) | | 20.3 | 20.3 | 16.5 | 17.3 | 16.8 | 27 |
| (A3) | (A3-1) Linear SBS (St %: 43%, diblock: 70%), TV: 360 mPas | | | | 4 | 3 | | |
| | (A3-2) Linear SBS (St %: 43%, diblock: 60%), TV: 170 mPas | | | | | | 4 | |
| | (A3-3) Linear SIS (St %: 24%, diblock: 67%), TV: 320 mPas | | | | | | | |
| (A4) | (A4-1) Three branched radial SBS (St: 35%, diblock: 40%), TV: 490 mPas | | | | | | | |
| | (A4-2) Three branched radial SIS (St: 25%, diblock: 40%), TV: 380 mPas | | | | | | | |
| | Total weight of (A) | | 20.3 | 20.3 | 20.5 | 20.3 | 20.8 | 27 |
| (B) | (B1) Tackifier resin (hydrogenated), Softening point: 100° C. | | 14 | 14 | 9 | 14 | 14 | 24 |
| | (B2) Tackifier resin (hydrogenated), Softening point: 100° C. | | | | | | | |
| | (B3) Tackifier resin (hydrogenated), Softening point: 115° C. | | | | | | | |
| | (B4) Tackifier resin (hydrogenated), Softening point: 100° C. | | 45 | 45 | 45.6 | 45 | 44.5 | |
| | (B5) Tackifier resin (hydrogenated), Softening point: 110° C. | | | | | | | |
| | (B6) Tackifier resin (hydrogenated), Softening point: 100° C. | | | | | | | 23.3 |
| | (B7) Tackifier resin (unhydrogenated), Softening point: 100° C. | | | | | | | 5 |
| | (B8) Tackifier resin (unhydrogenated), Softening point: 95° C. | | | | 4.5 | | | |
| | (B9) Tackifier resin (hydrogenated), Softening point: 115° C. | | | | | | | |
| | (B10) Tackifier resin (liquid) | | | | | | | |
| (C) | (C1) Paraffin oil | | 20 | 20 | 19.7 | 20 | 20 | 15 |
| | (C2) Naphthene oil | | | | | | | 5 |
| | (C3) Naphthene oil | | | | | | | |
| (D) | (D1) Phenol primary antioxidants | | 0.2 | 0.2 | 0.2 | 0.2 | 0.2 | 0.2 |
| | (D2) Sulfur secondary antioxidants | | 0.3 | 0.3 | 0.3 | 0.3 | 0.3 | 0.3 |
| | (D3) Ultraviolet absorber | | 0.2 | 0.2 | 0.2 | 0.2 | 0.2 | 0.2 |
| | (D4) Phenol primary antioxidants | | | | | | | |
| (E) | (E1) Maleic anhydride modified PP wax | | | | | | | |
| | Total weight of (A) to (E) | | 100 | 100 | 100 | 100 | 100 | 100 |

TABLE 2

|     |     |     | Example |     |     |     |
| --- | --- | --- | --- | --- | --- | --- |
|     |     |     | 7 | 8 | 9 | 10 |
| (A) |     |     |     |     |     |     |
| (A1) | (A1-1) Three branched radial SBS (St %: 38%, diblock: 80%), TV: 184 mPas |     |     | 4 |     |     |
|     | (A1-2) Three branched radial SBS (St %: 39%, diblock: 80%), TV: 165 mPas |     | 17 |   | 20 | 20 |
|     | (A1-3) Three branched radial SBS (St %: 43%, diblock: 70%), TV: 243 mPas |     | 2 |   |   |   |
| (A2) | (A2-1) Triblock SBS (St %: 40%, diblock: 0%), TV: 795 mPas |     | 3 | 12.3 | 2 |   |
|     | (A2-2) Triblock SBS (St %: 43%, diblock: 0%), TV: 688 mPas |     | 3 |   |   |   |
|     | (A2-3) Triblock SBS (St %: 30%, diblock: 0%), TV: 1200 mPas |     |   |   | 4 |   |
|     | (A2-4) Triblock SIS (St %: 44%, diblock: 0%), TV: 120 mPas |     |   |   |   |   |
|     | (A2-5) Triblock SIS (St %: 30%, diblock: 0%), TV: 300 mPas |     |   |   |   | 5 |
|     | Total weight of (A1) and (A2) |     | 25 | 16.3 | 26 | 25 |
| (A3) | (A3-1) Linear SBS (St %: 43%, diblock: 70%), TV: 360 mPas |     |   |   |   |   |
|     | (A3-2) Linear SBS (St %: 43%, diblock: 60%), TV: 170 mPas |     |   |   |   |   |
|     | (A3-3) Linear SIS (St %: 24%, diblock: 67%), TV: 320 mPas |     |   | 4 |   |   |
| (A4) | (A4-1) Three branched radial SBS (St: 35%, diblock: 40%), TV: 490 mPas |     |   |   |   |   |
|     | (A4-2) Three branched radial SIS (St: 25%, diblock: 40%), TV: 380 mPas |     |   |   |   |   |
|     | Total weight of (A) |     | 25 | 20.3 | 26 | 25 |
| (B) | (B1) Tackifier resin (hydrogenated), Softening point: 100° C. |     | 29.3 | 14 |   |   |
|     | (B2) Tackifier resin (hydrogenated), Softening point: 100° C. |     | 8 |   | 29 | 30 |
|     | (B3) Tackifier resin (hydrogenated), Softening point: 115° C. |     |   |   |   |   |
|     | (B4) Tackifier resin (hydrogenated), Softening point: 100° C. |     | 10 | 30 | 27.3 | 28.3 |
|     | (B5) Tackifier resin (hydrogenated), Softening point: 110° C. |     |   |   |   |   |
|     | (B6) Tackifier resin (hydrogenated), Softening point: 100° C. |     |   |   |   |   |
|     | (B7) Tackifier resin (unhydrogenated), Softening point: 100° C. |     |   |   |   |   |
|     | (B8) Tackifier resin (unhydrogenated), Softening point: 95° C. |     |   | 15 |   |   |
|     | (B9) Tackifier resin (hydrogenated), Softening point: 115° C. |     |   |   |   |   |
|     | (B10) Tackifier resin (liquid) |     | 10 |   |   |   |
| (C) | (C1) Paraffin oil |     |   | 20 | 16 | 16 |
|     | (C2) Naphthene oil |     | 17 |   |   |   |
|     | (C3) Naphthene oil |     |   |   |   |   |
| (D) | (D1) Phenol primary antioxidants |     | 0.2 | 0.2 | 0.2 | 0.2 |
|     | (D2) Sulfur secondary antioxidants |     | 0.3 | 0.3 | 0.3 | 0.3 |
|     | (D3) Ultraviolet absorber |     | 0.2 | 0.2 | 0.2 | 0.2 |
|     | (D4) Phenol primary antioxidants |     |   |   |   |   |
| (E) | (E1) Maleic anhydride modified PP wax |     |   |   |   | 1 |
|     | Total weight of (A) to (E) |     | 100 | 100 | 100 | 100 |

TABLE 3

|     |     | Comp. Ex. |     |     |     |     |     |
| --- | --- | --- | --- | --- | --- | --- | --- |
|     |     | 1 | 2 | 3 | 4 | 5 | 6 |
| (A) |     |   |   |   |   |   |   |
| (A1) | (A1-1) Three branched radial SBS (St %: 38%, diblock: 80%), TV: 184 mPas | 22 | 22 | 17 |   |   |   |
|     | (A1-2) Three branched radial SBS (St %: 39%, diblock: 80%), TV: 165 mPas |   |   |   |   |   |   |
|     | (A1-3) Three branched radial SBS (St %: 43%, diblock: 70%), TV: 243 mPas |   |   |   |   |   |   |
| (A2) | (A2-1) Triblock SBS (St %: 40%, diblock: 0%), TV: 795 mPas |   |   |   | 10 |   |   |
|     | (A2-2) Triblock SBS (St %: 43%, diblock: 0%), TV: 688 mPas |   |   |   | 10 |   |   |
|     | (A2-3) Triblock SBS (St %: 30%, diblock: 0%), TV: 1200 mPas |   |   |   |   |   |   |

TABLE 3-continued

|  |  | Comp. Ex. | | | | | |
|---|---|---|---|---|---|---|---|
|  |  | 1 | 2 | 3 | 4 | 5 | 6 |
|  | (A2-4) Triblock SIS (St %: 44%, diblock: 0%), TV: 120 mPas | | | | | | |
|  | (A2-5) Triblock SIS (St %: 30%, diblock: 0%), TV: 300 mPas | | | | | | |
|  | Total weight of (A1) and (A2) | 22 | 22 | 17 | 20 | 0 | 0 |
| (A3) | (A3-1) Linear SBS (St %: 43%, diblock: 70%), TV: 360 mPas | | | | | | |
|  | (A3-2) Linear SBS (St %: 43%, diblock: 60%), TV: 170 mPas | | 5 | 10 | | 24.8 | |
|  | (A3-3) Linear SIS (St %: 24%, diblock: 67%), TV: 320 mPas | | | | | | |
| (A4) | (A4-1) Three branched radial SBS (St: 35%, diblock: 40%), TV: 490 mPas | 5 | | | | | 19.9 |
|  | (A4-2) Three branched radial SIS (St: 25%, diblock: 40%), TV: 380 mPas | | | | | | 9.9 |
|  | Total weight of (A) | 27 | 27 | 27 | 20 | 24.8 | 29.8 |
| (B) | (B1) Tackifier resin (hydrogenated), Softening point: 100° C. | 42.3 | 42.3 | 42.3 | | 49.6 | |
|  | (B2) Tackifier resin (hydrogenated), Softening point: 100° C. | 14 | 14 | 14 | 40 | | 49.6 |
|  | (B3) Tackifier resin (hydrogenated), Softening point: 115° C. | | | | | | |
|  | (B4) Tackifier resin (hydrogenated), Softening point: 100° C. | | | | | | |
|  | (B5) Tackifier resin (hydrogenated), Softening point: 110° C. | | | | 19.3 | | |
|  | (B6) Tackifier resin (hydrogenated), Softening point: 100° C. | | | | | | |
|  | (B7) Tackifier resin (unhydrogenated), Softening point: 100° C. | | | | | | |
|  | (B8) Tackifier resin (unhydrogenated), Softening point: 95° C. | | | | | | |
|  | (B9) Tackifier resin (hydrogenated), Softening point: 115° C. | | | | | | |
|  | (B10) Tackifier resin (liquid) | | | | | 19.9 | |
| (C) | (C1) Paraffin oil | 15 | 15 | 15 | 8 | 5 | |
|  | (C2) Naphthene oil | | | | 10 | | 19.9 |
|  | (C3) Naphthene oil | | | | | | |
| (D) | (D1) Phenol primary antioxidants | 0.2 | 0.2 | 0.2 | 0.2 | 0.2 | 0.2 |
|  | (D2) Sulfur secondary antioxidants | 0.3 | 0.3 | 0.3 | 0.3 | 0.3 | 0.3 |
|  | (D3) Ultraviolet absorber | 0.2 | 0.2 | 0.2 | 0.2 | 0.2 | 0.2 |
|  | (D4) Phenol primary antioxidants | | | | | | |
| (E) | (E1) Maleic anhydride modified PP wax | | | | | | |
|  | Total weight of (A) to (E) | 100 | 100 | 100 | 100 | 100 | 100 |

TABLE 4

|  |  | Comp. Ex. | |
|---|---|---|---|
|  |  | 7 | 8 |
| (A) | | | |
| (A1) | (A1-1) Three branched radial SBS (St %: 38%, diblock: 80%), TV: 184 mPas | | |
|  | (A1-2) Three branched radial SBS (St %: 39%, diblock: 80%), TV: 165 mPas | | |
|  | (A1-3) Three branched radial SBS (St %: 43%, diblock: 70%), TV: 243 mPas | | |
| (A2) | (A2-1) Triblock SBS (St %: 40%, diblock: 0%), TV: 795 mPas | | |
|  | (A2-2) Triblock SBS (St %: 43%, diblock: 0%), TV: 688 mPas | | |
|  | (A2-3) Triblock SBS (St %: 30%, diblock: 0%), TV: 1200 mPas | | |
|  | (A2-4) Triblock SIS (St %: 44%, diblock: 0%), TV: 120 mPas | | 20 |
|  | (A2-5) Triblock SIS (St %: 30%, diblock: 0%), TV: 300 mPas | 17.9 | |
|  | Total weight of (A1) and (A2) | 17.9 | 20 |
| (A3) | (A3-1) Linear SBS (St %: 43%, diblock: 70%), TV: 360 mPas | | |
|  | (A3-2) Linear SBS (St %: 43%, diblock: 60%), TV: 170 mPas | | |
|  | (A3-3) Linear SIS (St %: 24%, diblock: 67%), TV: 320 mPas | | |

TABLE 4-continued

| | | Comp. Ex. | |
|---|---|---|---|
| | | 7 | 8 |
| (A4) | (A4-1) Three branched radial SBS (St: 35%, diblock: 40%), TV: 490 mPas | | |
| | (A4-2) Three branched radial SIS (St: 25%, diblock: 40%), TV: 380 mPas | | |
| | Total weight of (A) | 17.9 | 20 |
| (B) | (B1) Tackifier resin (hydrogenated), Softening point: 100° C. | | |
| | (B2) Tackifier resin (hydrogenated), Softening point: 100° C. | | |
| | (B3) Tackifier resin (hydrogenated), Softening point: 115° C. | 59.6 | |
| | (B4) Tackifier resin (hydrogenated), Softening point: 100° C. | | |
| | (B5) Tackifier resin (hydrogenated), Softening point: 110° C. | | |
| | (B6) Tackifier resin (hydrogenated), Softening point: 100° C. | | |
| | (B7) Tackifier resin (unhydrogenated), Softening point: 100° C. | | |
| | (B8) Tackifier resin (unhydrogenated), Softening point: 95° C. | | |
| | (B9) Tackifier resin (hydrogenated), Softening point: 115° C. | | 57.8 |
| | (B10) Tackifier resin (liquid) | | |
| (C) | (C1) Paraffin oil | | |
| | (C2) Naphthene oil | | |
| | (C3) Naphthene oil | 22 | 21.7 |
| (D) | (D1) Phenol primary antioxidants | | |
| | (D2) Sulfur secondary antioxidants | | |
| | (D3) Ultraviolet absorber | | |
| | (D4) Phenol primary antioxidants | 0.5 | 0.5 |
| (E) | (E1) Maleic anhydride modified PP wax | | |
| | Total weight of (A) to (E) | 100 | 100 |

With respect to the thus obtained hot-melt adhesive agents of Example and Comparative Examples, properties of a melt viscosity, a peel strength, a retention force, loop tackiness were examined. The results are shown in Tables 5 to 7. The above properties were investigated by the following methods.

Melt Viscosity

A hot-melt adhesive agent was melted by heating at 120° C. and 140° C., and then a viscosity in a molten state was measured using a Brookfield RVT type viscometer (spindle No. 27). Evaluation criteria are as follows.

| A | Viscosity at 120° C. is not more than 10,000 mPa · s |
| B | Viscosity at 120° C. is more than 10,000 mPa · s and not more than 20,000 mPa · s |
| C | Viscosity at 120° C. is more than 20,000 mPa · s |

| A | Viscosity at 140° C. is not more than 4,000 mPa · s |
| B | Viscosity at 140° C. is more than 4,000 mPa · s and not more than 5,000 mPa · s |
| C | Viscosity at 140° C. is more than 5,000 mPa · s |

Peel Strength hot-melt adhesive agent was applied to a 50 μm thick PET film in a thickness of 50 μm. The coated PET film was formed into 2.5 cm wide strips to obtain specimens. Each specimen was laid on a 100 μm thick polyethylene film at 20° C., followed by being left to stand at 20° C. for 1 day. Thereafter, peeling was performed at 10° C., 20° C., 40° C. at a tension speed of 300 mm/minute and the peel strength was measured.

| A | Peel strength is more than 1,400 (g/25 mm) |
| B | Peel strength is 1,200 (g/25 mm) to 1,400 (g/25 mm) |
| C | Peel strength is less than 1,200 (g/25 mm) |

Retention Force

A hot-melt adhesive agent was applied to a 50 μm thick PET film in a thickness of 50 μm. The coated PET film was formed into a size measuring 2.5 cm in width to obtain specimens. A PET film in a thickness of 50 μm was applied to the specimen at 20° C. so that the contact area was 1.0 cm×2.5 cm. A weight of 1 kg was hung to the polyethylene film in the direction perpendicular to the contact surface, and left under the condition of 40° C. The time elapsed before the weight of 1 kg fell was measured, and it was adopted as the retention force.

| A | Retention force is over 50 minutes |
| B | Retention force is 10 minutes to 50 minutes |
| C | Retention force is less than 10 minutes |

Loop Tackiness

A hot-melt adhesive agent was applied to a 50 μm thick PET film in a thickness of 50 μm. The coated PET film was formed into a size measuring 2.5 cm×10 cm to obtain specimens. Each specimen was wound in a loop form so that an adhesive surface (surface to be coated with an adhesive agent) faces outside, and then the loop was brought into contact with a PE sheet at 20° C. at a speed of 300 mm/minute. Then, the specimen was peeled from the PE sheet at a speed of 300 mm/minute to thereby measure the peel strength at the time of peeling, which was regarded as loop tackiness.

| | |
|---|---|
| A | Loop tackiness is more than 2,200 (g/25 mm) |
| B | Loop tackiness is 2,000 (g/25 mm) to 2,200 (g/25 mm) |
| C | Loop tackiness is less than 2,000 (g/25 mm) |

TABLE 5

| | | Example | | | | | |
|---|---|---|---|---|---|---|---|
| Condition | | 1 | 2 | 3 | 4 | 5 | 6 |
| Melt viscosity (mPas) | 120° C. | 7850<br>A | 6800<br>A | 9050<br>A | 8900<br>A | 8130<br>A | 15900<br>B |
| | 140° C. | 3000<br>A | 2630<br>A | 3380<br>A | 3380<br>A | 3060<br>A | 3990<br>A |
| PE Peel strength (g/25 mm) | 10° C. | 2610<br>A | 2480<br>A | 2500<br>A | 2640<br>A | 2630<br>A | 2000<br>A |
| | 20° C. | 1850<br>A | 1750<br>A | 1800<br>A | 1790<br>A | 1860<br>A | 1410<br>A |
| | 40° C. | 1400<br>A | 1330<br>B | 1400<br>A | 1380<br>B | 1400<br>A | 1230<br>B |
| Loop tack (g/25 mm) | | 2370<br>A | 2360<br>A | 2340<br>A | 2250<br>A | 2420<br>A | 2280<br>A |
| Retention force (min) | vsPET | 66<br>A | 52<br>A | 43<br>B | 30<br>B | 34<br>B | 46<br>B |

TABLE 6

| | | Example | | | |
|---|---|---|---|---|---|
| Condition | | 7 | 8 | 9 | 10 |
| Melt viscosity (mPas) | 120° C. | 9830<br>A | 9350<br>A | 16600<br>B | 10800<br>B |
| | 140° C. | 3280<br>A | 3410<br>A | 4960<br>B | 3380<br>A |
| PE Peel strength (g/25 mm) | 10° C. | 2190<br>A | 2550<br>A | 2380<br>A | 2230<br>A |
| | 20° C. | 1430<br>A | 1830<br>A | 1650<br>A | 1350<br>B |
| | 40° C. | 1280<br>B | 1450<br>A | 1230<br>B | 1240<br>B |
| Loop tack (g/25 mm) | | 2710<br>A | 2220<br>A | 2560<br>A | 2700<br>A |
| Retention force (min) | vsPET | 35<br>B | 36<br>B | 100<br>A | 61<br>A |

TABLE 7

| | | Comp. Example | | | | | |
|---|---|---|---|---|---|---|---|
| Condition | | 1 | 2 | 3 | 4 | 5 | 6 |
| Melt viscosity (mPas) | 120° C. | 13400<br>B | 11800<br>B | 11800<br>B | 20000<br>C | 8360<br>A | 36900<br>C |
| | 140° C. | 4790<br>B | 4060<br>B | 4060<br>B | 6500<br>C | 2650<br>A | 12900<br>C |
| PE Peel strength (g/25 mm) | 10° C. | 2230<br>A | 2300<br>A | 2260<br>A | 20<br>C | 1020<br>C | 2660<br>A |
| | 20° C. | 1550<br>A | 1480<br>A | 1560<br>A | 590<br>C | 1840<br>A | 1590<br>A |
| | 40° C. | 1180<br>C | 1050<br>C | 1100<br>C | 1460<br>A | 1180<br>C | 1040<br>C |
| Loop tack (g/25 mm) | | 2430<br>A | 2920<br>A | 2870<br>A | 270<br>C | 3330<br>A | 2180<br>B |
| Retention force (min) | vsPET | 268<br>A | 172<br>A | 165<br>A | 84<br>A | 250<br>A | more than 1440<br>A |

TABLE 8

| | | Comp. Example | |
|---|---|---|---|
| Condition | | 7 | 8 |
| Melt viscosity (mPas) | 120° C. | 10650<br>B | 12800<br>B |
| | 140° C. | 3400<br>A | 3340<br>A |
| PE Peel strength (g/25 mm) | 10° C. | 105<br>C | 79<br>C |
| | 20° C. | 1310<br>B | 325<br>C |
| | 40° C. | 1500<br>A | 1540<br>A |
| Loop tack (g/25 mm) | | 1130<br>C | 430<br>C |
| Retention force (min) | vsPET | 142<br>A | more than 1440<br>A |

As shown in Tables 5 to 8, the hot-melt adhesive agents of Examples are excellent in melt viscosity (application property at low temperature), adhesiveness at 10 to 40° C. (softening point), retention force and loop tackiness since they include both the components (A1) and (A2). To the contrary, the hot-melt adhesive agents of Comparative Examples are significantly inferior in any one of the respective performances as compared with the hot-melt adhesive agents of Examples since they do not include either the component (A1) or (A2).

They were proved that, by inclusion of both the components (A1) and (A2), the hot-melt adhesive agent is improved in adhesiveness in the wide temperature range at 10° C. to 40° C., it is suitable to be applied under low temperature, and it is excellent in balance between tackiness and retention force. When a disposable product is produced, the hot-melt adhesive agent of the present invention is able to be applied at a low temperature of not more than 140° C. It was demonstrated as to disposable products that each of parts of the disposable product hardly peels off at a low temperature in the winter season, during storage in warehouse at summer season, or under a body temperature as the disposable product is on use.

INDUSTRIAL APPLICABILITY

The present invention provides a hot-melt adhesive agent, and a disposable product which is obtained by applying the hot-melt adhesive agent. The hot-melt adhesive agent according to the present invention is particularly suitable for the production of a disposable product.

The invention claimed is:

1. A hot-melt adhesive agent comprising a mixture of
   (A1) a radial type styrene block copolymer having a styrene content of 35 to 45% by weight, a diblock content of 50 to 90% by weight, and has a viscosity at 25° C. as 25% toluene solution of not more than 250 mPa·s; and
   (A2) a triblock type styrene block copolymer having 0% diblock content and a styrene content of 30 to 45% by weight; and
   wherein a linear styrene block copolymer not including A2 is optionally present and wherein any linear styrene block copolymer present not including A2 has 50-90% by weight diblock content; and
   wherein the hot-melt adhesive agent has a melt viscosity at 140° C. of less than 4000 mPa·s.

2. The hot-melt adhesive agent according to claim 1, wherein the radial type styrene block copolymer (A1) comprises a three branched type styrene-butadiene block copolymer.

3. A disposable product comprising the hot-melt adhesive agent according to claim 1.

4. The disposable product according to claim 3, which is paper diaper, a sanitary napkin, a pet sheet, a hospital gown or a surgical white garment.

* * * * *

UNITED STATES PATENT AND TRADEMARK OFFICE
CERTIFICATE OF CORRECTION

PATENT NO. : 10,017,672 B2
APPLICATION NO. : 14/944526
DATED : July 10, 2018
INVENTOR(S) : Masahiro Moriguchi and Naohiro Maeda It is certified that error appears in the above-identified patent and that said Letters Patent is hereby corrected as shown below:

In the Specification

Column 8, Line 41, change "law" to "low"

Signed and Sealed this
Eighth Day of January, 2019

Andrei Iancu
*Director of the United States Patent and Trademark Office*